United States Patent
Kawabe et al.

(10) Patent No.: US 7,034,011 B2
(45) Date of Patent: Apr. 25, 2006

(54) METHOD OF STABILIZING REDUCED NICOTINAMIDE ADENINE DINUCLEOTIDE OR REDUCED NICOTINAMIDE ADENINE DINUCLEOTIDE PHOSPHATE

(75) Inventors: Hideo Kawabe, Saitama (JP); Hideki Murata, Hofu (JP); Hiroshi Nagano, Hofu (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/502,922

(22) PCT Filed: Dec. 3, 2003

(86) PCT No.: PCT/JP03/15482

§ 371 (c)(1),
(2), (4) Date: Jul. 28, 2004

(87) PCT Pub. No.: WO2004/050099

PCT Pub. Date: Jun. 17, 2004

(65) Prior Publication Data

US 2005/0119199 A1  Jun. 2, 2005

(30) Foreign Application Priority Data

Dec. 3, 2002  (JP) .............................. 2002-350813

(51) Int. Cl.
*A61K 31/70* (2006.01)
*C07H 19/207* (2006.01)

(52) U.S. Cl. ........................... 514/45; 514/46; 514/47; 514/23; 536/26.24; 536/1.11

(58) Field of Classification Search ............... 514/45, 514/46, 47, 23; 536/26.24, 1.11
See application file for complete search history.

(56) References Cited

U.S. PATENT DOCUMENTS

| 5,019,561 A | 5/1991 | Birkmayer |
| 5,332,727 A | 7/1994 | Birkmayer |
| 5,444,053 A | 8/1995 | Birkmayer |
| 5,668,114 A | 9/1997 | Birkmayer |

FOREIGN PATENT DOCUMENTS

| EP | 1 083 235 | 3/2001 |
| JP | 2002-017295 | 1/2002 |

OTHER PUBLICATIONS

Nakagawa et al. (Journal of nutritional science and vitaminology, (Jun. 1997) 43(3) 345-55) (Abstract Sent).*
Cyto-protection and Biology, vol. 7, 1989, pp. 383-391.
Duran et al., "Actividad Antioxidante de las Vitaminas C y E y de la Provitimina A", *Grasas y Aceites*, vol. 44, No. 2, 1993, pp. 107-111.
Jyonouchi et al., "Immunomodulating Actions of Carotenoids: Enhancement of In Vivo and In Vitro Antibody Production to T-Dependent Antigens", *Nutrition and Cancer*, vol. 21, 1994, pp. 47-58.

* cited by examiner

*Primary Examiner*—Michael C. Henry
(74) *Attorney, Agent, or Firm*—Fitzpatrick, Cella, Harper & Scinto

(57) ABSTRACT

It is an object of the present invention to provide a method of stabilizing reduced nicotinamide adenine dinucleotide or reduced nicotinamide adenine dinucleotide phosphate [hereinafter abbreviated as NAD(P)H] and a preparation containing NAD(P)H stabilized by the method.

As the method of stabilizing NAD(P)H, a method of adding astaxanthin to NAD(P)H is provided.

9 Claims, No Drawings

METHOD OF STABILIZING REDUCED NICOTINAMIDE ADENINE DINUCLEOTIDE OR REDUCED NICOTINAMIDE ADENINE DINUCLEOTIDE PHOSPHATE

TECHNICAL FIELD

The present invention relates to a method of stabilizing reduced nicotinamide adenine dinucleotide (hereinafter abbreviated as NADH) or reduced nicotinamide adenine dinucleotide phosphate (hereinafter abbreviated as NADPH) and a preparation containing NADH or NADPH [hereinafter abbreviated as NAD(P)H].

BACKGROUND ART

NADH is known to be effective for hypertension (U.S. Pat. No. 5,668,114), Parkinson's disease (U.S. Pat. No. 5,019,561) and Alzheimer disease (U.S. Pat. No. 5,444,053). Also NADPH is known to be effective for hypertension (U.S. Pat. No. 5,668,114) and Parkinson's disease (U.S. Pat. No. 5,019,561).

NAD(P)H has been widely used for preventive supplements (auxiliary nutritional agents) for these adult diseases.

However, since NAD(P)H is unstable at ambient temperature, it have been prevalent that means to formulate the NAD(P)H are taken.

Addition of a stabilizer such as polyvinylpyrrolidone, sodium hydrogen carbonate, tocopherol and ascorbic acid to a preparation containing NAD(P)H in order to enhance stability of NAD(P)H was reported (U.S. Pat. No. 5,332,727).

However, as to polyvinylpyrrolidone there is a problem in that a safety zone is narrow. Thus, polyvinylpyrrolidone can be orally ingested only up to 120 mg per day in adults. Sodium hydrogen carbonate possibly influences pH of the preparation. Tocopherol is oil and thus is difficult to formulate. Also, there is a problem in that ascorbic acid give a taste to tablets.

Therefore, development in methods capable of stabilizing NAD(P)H with a small added amount of a substance without influencing the preparation has been demanded.

Astaxanthin has been widely used for supplements because it acts to prevent biological membrane disorder (Cyto-protect Biochem., 7:383–391, 1989) and has an immunoregulatory function (Nutr. Cancer, 21:47–58, 1994) due to its strong free radical. However, the action of astaxanthin to stabilize NAD(P)H has not been known.

DISCLOSURE OF THE INVENTION

An object of the present invention is to provide a method of stabilizing NAD(P)H and a preparation containing stabilized NAD(P)H.

The present invention relates to the following (1) to (8).

(1) A method of stabilizing NAD(P)H, which comprises adding astaxanthin to NAD(P)H.

(2) A method of stabilizing NAD(P)H in a preparation containing NAD(P)H, which comprises having astaxanthin included in a preparation containing NAD(P)H.

(3) The method according to (1) or (2), wherein the amount of astaxanthin is from 0.01 to 150 parts by weight based on 100 parts by weight of NAD(P)H.

(4) The method according to (1) or (2), wherein the amount of astaxanthin is from 1 to 20 parts by weight based on 100 parts by weight of NAD(P)H.

(5) A preparation, which comprises astaxanthin and NAD(P)H.

(6) The preparation according to (5), wherein astaxanthin is included in 0.01 to 150 parts by weight based on 100 parts by weight of NAD(P)H.

(7) The preparation according to (5), wherein astaxanthin is included in 1 to 20 parts by weight based on 100 parts by weight of NAD(P)H.

(8) The preparation according to any one of (5) to (7), wherein the preparation is in a form of a sublingual tablet, an enteric coated tablet or an enteric coated capsule.

NAD(P)H used for the present invention may be a free body or a pharmaceutically acceptable salt thereof.

The salts include alkali metal salts such as sodium salt and potassium salt, inorganic acid salts such as hydrochloride, sulfate and phosphate salts, and organic acid salts such as acetate, maleate, fumarate, citrate, lactate and methanesulfonate.

Astaxanthin used for the present invention may be either one obtained from nature or one obtained by a chemosynthetic method, and may be a purified product or a partially purified product. Commercially available ones can be used.

For example, an ester body of astaxanthin derived from blue-green algae or amur adonis, a free body of astaxanthin obtained by culturing yeast or by a chemosynthetic method and the like are included.

NAD(P)H can be stabilized by adding astaxanthin to NAD(P)H. NAD(P)H may present as it is or in a state of being contained in a preparation.

An amount of astaxanthin to be added is not particularly defined, but is preferably 0.01 parts by weight or more, more preferably from 0.01 to 150 parts by weight, and particularly preferably from 1 to 20 parts by weight based on 100 parts by weight of NAD(P)H.

The preparation of the present invention is the preparation containing NAD(P)H and astaxanthin, and is produced by mixing these substances with bases for preparation to be typically used in the pharmaceutical or food field if necessary, by any methods known in the technical field of pharmaceutics.

The bases for preparation include the following excipients, disintegrants, binders, lubricants and the like.

The excipients include lactose, maltose, trehalose, mannitol, reduced maltose starch syrup, lactitol, xylitol, sorbitol, erythritol and the like. These substances can be used alone or in combination.

The disintegrants include carboxymethylcellulose, calcium carboxymethylcellulose, sodium carboxymethylcellulose, crospovidone, sodium croscarmellose, starch sodium glycolate, starch, and the like. These substances can be used alone or in combination.

The binders include polyvinylpyrrolidone, pullulan, methylcellulose, hydroxypropylcellulose, polyvinyl alcohol, gelatin, agar, and the like. These substances can be used alone or in combination.

The lubricants include sucrose fatty acid ester, magnesium stearate, calcium stearate, sodium stearyl fumarate, and the like.

In addition to the above bases for preparations, hydrocarbon such as dextrin, an agent for correcting bitter such as cyclodextrin, pigments for food such as β carotene, vitamins such as niacin, vitamin E, ascorbic acid, vitamins B, vitamin A and vitamin D, minerals such as sodium, sweeteners such as aspartame, glucose, fructose, sucralose, stevia and saccharose, a desiccant such as fine silicon dioxide, and anti-caking agents such as calcium silicate, synthetic aluminium silicate and talc may be added if necessary.

The proportion of NAD(P)H in the preparation of the present invention is preferably from 0.01 to 90 parts by weight, more preferably from 0.1 to 50 parts by weight, and still more preferably from 1 to 30 parts by weight based on 100 parts by weight of the preparation. NAD(P)H may be in a form of any of liquid, powdery, granular, powdery granular and the like.

An amount of astaxanthin in the preparation of the present invention is not particularly defined, but is preferably 0.01 parts by weight or more, more preferably from 0.01 to 150 parts by weight, and still more preferably from 1 to 20 parts by weight based on 100 parts by weight of NAD(P)H in the preparation. Astaxanthin maybe in a form of any of liquid, powdery, granular, powdery granular and the like.

For preventing NAD(P)H from being decomposed in stomach, it is preferred that the preparation of the present invention is made to be a formulation such as suppository, sublingual tablet, enteric coated tablet or enteric coated capsule. The sublingual tablet, enteric coated tablet or enteric coated capsule are preferred, and the enteric coated tablet or enteric coated capsule which are easy to take are particularly preferred.

The preparation of the present invention is intended to supply NAD(P)H and is used as pharmaceuticals or healthy foods for human or non-human.

When the preparation of the present invention is produced as an enteric coated capsule, it is possible to produce the preparation as a soft capsule or a hard capsule by conventional methods.

As an example, a process for producing the enteric coated hard capsule is shown below.

An excipient in an amount of 2 to 4.0 times (weight ratio) relative to the NAD(P)H is added, 0.01 parts by weight or more of astaxanthin based on 100 parts by weight of NAB(P)H is added thereto, and the mixture is stirred to yield a powder for the preparation of the present invention. A desiccant such as fine silicon dioxide in 2 parts by weight or less based on 100 parts by weight of the powder may be added if necessary. The resultant powder for the preparation of the present invention is applied to a capsule filling machine and filled into a hard capsule. The hard capsule in which the powder for the preparation of the present invention is filled is sealed up by sealing by a conventional method if necessary. Furthermore, an enteric coated capsule can be produced by coating a surface of the hard capsule in which the powder is filled with a base agent such as shellac solution, zein solution, and cellulose acetate typically used for the production of enteric coated agents by conventional methods.

When the preparation of the present invention is produced as a sublingual tablet or an enteric coated tablet, the tablets can be produced by conventional methods, for example, by incorporating a powdery granular body containing NAD (P)H and astaxanthin into a tablet.

The powdery granular body containing NAD(P)H and astaxanthin may comprise the above excipient, disintegrant, binder, lubricant or other additive ingredients in addition to NAD(P)H and astaxanthin.

As the method of producing the tablets, mention may be made of a method for compression molding of the powdery granular body containing NAD(P)H and astaxanthin according to a tableting method and a method for wet granulation or dry granulation of whole or a part of the powdery granular body followed by compression molding.

As the tableting method, for example, a conventional method for compression molding after adding and mixing the powdery granular body according to need, a method previously applying a lubricant on a surface of the pestle and mortar wall followed by compression molding of the powdery granular body, and the like are used.

An apparatus used for the dry granulation includes, for example, a cracking granulator and the like.

Apparatuses used for the wet granulation include, for example, a stirring granulator, a fluidized bed granulator, extrusion granulator, a rolling fluidized bed granulator, and the like.

The sublingual tablet can be produced by, for example, tableting with lower pressure than the case of regular tablets in a process for producing regular tablets.

The enteric coated tablet can be produced by coating the surface of the tablet obtained by compression molding with the basis such as shellac solution, zein solution, and cellulose acetate typically used in the production of enteric coating by conventional methods using a coating pan.

The process for producing the preparation of the present invention is not limited to the above methods, and it is possible to use any methods so long as they are methods capable of formulating the product.

In the preparation of the present invention, the NAD(P)H contained in the preparation is kept stable because of astaxanthin which is included, and thus the preparation can effectively act as an auxiliary nutritional agent in vivo.

A dosage of the preparation of the present invention varies depending on the type of administration to human or non-human, age, body weight, conditions and the like. For example, when used as a preventive supplement for adult diseases of humans such as hypertension, Parkinson's disease and Alzheimer disease, a preparation comprising 5 to 1500 mg, preferably from 20 to 30 mg, of NAD(P)H, is orally administered 1 to 3 times per day to an adult.

BEST MODE FOR CARRYING OUT THE INVENTION

EXAMPLE 1

Fifty grams of NADH (supplied by Kyowa Hakko Kogyo Co. Ltd.), 500 g of astaxanthin (containing 1% by weight of ester derived from blue-green algae; supplied by Fuji Chemical Co. Ltd.) and 450 g of mannitol (supplied by Nikken Chemical and Synthetic Industry Co. Ltd.) were mixed and stirred. The mixture was placed in a capsule filling machine, and filled into, 5000 tablets of hard capsules No. 2 made of gelatin. The resultant hard capsule was coated with zein solution to prepare an enteric coated capsule (Capsule 1) containing 10 mg of NADH and 1 mg of astaxanthin.

EXAMPLE 2

Two hundred grams of NADH (supplied by Kyowa Hakko Kogyo Co. Ltd.), 200 g of astaxanthin (containing 1% by weight of ester derived from blue-green algae; supplied by Fuji Chemical Co. Ltd.), 3560 g of mannitol (supplied by Nikken Chemical and Synthetic Industry Co. Ltd.) and 40 g of silica dioxide were mixed and stirred. The mixture was placed in a capsule filling machine, and filled into 20000 tablets of hard capsules No. 2 made of gelatin. The resultant hard capsule was coated with zein solution to prepare an enteric coated capsule containing 10 mg of NADH and 0.1 mg of astaxanthin.

COMPARATIVE EXAMPLE 1

Fifty grams of NADH (supplied by Kyowa Hakko Kogyo Co. Ltd.), 50 g of polyvinylpyrrolidone K25 (supplied by Gokyo Trading Co. Ltd.) and 900 g of mannitol (supplied by Nikken. Chemical and Synthetic Industry Co. Ltd.) were mixed and stirred. The mixture was placed in a capsule filling machine, and filled into 5000 tablets of hard capsules No. 2 made of gelatin. The resultant hard capsule was coated with zein solution to prepare an enteric coated capsule (Capsule a) containing 10 mg of NADH and 10 mg of polyvinylpyrrolidone K25.

EXAMPLE 3

Capsules 1 prepared in Examples 1 and Capsule a prepared in Comparative example 1 were separately placed into glass bottles. After sealing and shielding the light, the bottles were stored at 60° C. for 33 hours. The stored capsules were opened at the start of the storage, at 14 and 33 hours after the start of the storage, and each of the samples was dissolved in 10 mmol/l of $Na_2CO_3$ buffer (pH 10).

Each solution was filtered trough a membrane filter (0.45 μm), and subsequently, the absorbance was measured at 340 nm using a model U-3210 self-recording spectrometer (supplied by Hitachi Ltd.). Based on the absorbance at the start of the storage defined as 100%, the values of the absorbance at 14 and 33 hours after the start of the storage were calculated, which were rendered a residual ratio of NADH.

The results are shown in Table 1.

TABLE 1

| Capsule No. | Residual rate of NADH (%) | |
| --- | --- | --- |
|  | in 14 hours | in 33 hours |
| 1 | 78.4 | 83.2 |
| a | 47.5 | 13.3 |

According to Table 1, in Capsule 1 containing 1 mg of astaxanthin, the residual ratio of NADH was about 80% even though it was stored in the harsh conditions for 33 hours. On the other hand, in Capsule a, the residual ratios were about 50% at 14 hours of the storage and about 13% at 33 hours, and NADH was obviously decomposed despite of addition of 10 mg of polyvinylpyrrolidone K25 as a stabilizer.

As shown above, the residual ratio of NADH in the capsule with the addition of astaxanthin was obviously higher compared to that in the capsule with the addition of polyvinylpyrrolidone K25.

INDUSTRIAL APPLICABILITY

According to the present invention, a method of stabilizing NAD(P)H and a preparation containing stabilized NAD (P)H are provided.

The invention claimed is:

1. A preparation which comprises axtaxanthin and NAD(P)H, and is in a form of a sublingual tablet, an enteric coated tablet or an enteric coated capsule.

2. A preparation which comprises astaxanthin, NAD(P)H and mannitol.

3. A preparation which comprises astaxanthin, NAD(P)H and silicon dioxide.

4. A preparation which comprises astaxanthin, NAD(P)H, mannitol and silicon dioxide.

5. The preparation according to any one of claims 1–4, wherein astaxanthin is contained amount of 0.01 to 150 parts by weight based on 100 parts by weight of NAD(P)H.

6. The preparation according to claim 5, wherein astaxanthin is contained in the amount of 1 to 20 parts by weight based on 100 parts by weight of NAD(P)H.

7. The preparation according to any one of claims 2–4, which is in the form of a sublingual tablet, an enteric coated tablet or an enteric coated capsule.

8. The preparation according to claim 7, wherein astaxanthin is contained in the amount of 0.01 to 150 parts by weight based on 100 parts by weight of NAD(P)H.

9. The preparation according to claim 8, wherein astaxanthin is contained in the amount of 1 to 20 parts by weight based on 100 parts by weight of NAD(P)H.

* * * * *

UNITED STATES PATENT AND TRADEMARK OFFICE
CERTIFICATE OF CORRECTION

PATENT NO. : 7,034,011 B2
APPLICATION NO. : 10/502922
DATED : April 25, 2006
INVENTOR(S) : Hideo Kawabe et al.

It is certified that error appears in the above-identified patent and that said Letters Patent is hereby corrected as shown below:

COLUMN 1
　　　　Line 19, "Alzheimer" should read --Alzheimer's--;
　　　　Line 26, "have" should read --has--; and
　　　　Line 38, "give" should read –contributes--.

COLUMN 4
　　　　Line 33, "Alzheimer" should read --Alzheimer's--; and
　　　　Line 49, "into," should read --into--.

COLUMN 5
　　　　Line 42, "the" should be deleted.

COLUMN 6
　　　　Line 4, "of" (first occurrence) should be deleted;
　　　　Line 17, "axtaxanthin" should read --astaxanthin--; and
　　　　Line 27, "amount" should read --in the amount--.

Signed and Sealed this

Twenty-first Day of November, 2006

JON W. DUDAS
*Director of the United States Patent and Trademark Office*